(12) United States Patent
Jaeger (10) Patent No.: US 6,792,818 B2
(45) Date of Patent: Sep. 21, 2004

(54) LIQUID SAMPLER HAVING AN IN-LINE VALVE

(76) Inventor: Ben E. Jaeger, 50 Hunter La., Bristol, IL (US) 60512

( * ) Notice: Subject to any disclaimer, the term of this patent is extended or adjusted under 35 U.S.C. 154(b) by 0 days.

(21) Appl. No.: 10/118,477

(22) Filed: Apr. 8, 2002

(65) Prior Publication Data

US 2003/0188588 A1 Oct. 9, 2003

(51) Int. Cl.[7] .............................................. G01N 11/00

(52) U.S. Cl. ............................. 73/863.86; 73/863.82; 73/863.85

(58) Field of Search ...................... 73/863.44, 863.72, 73/863.81–863.86

(56) References Cited

U.S. PATENT DOCUMENTS

| | | | |
|---|---|---|---|
| 3,007,340 A | | 11/1961 | Kraftson |
| 4,147,062 A | | 4/1979 | Jaeger |
| 4,262,533 A | | 4/1981 | Jaeger |
| 4,294,124 A | * | 10/1981 | Kalwaitis ................. 73/863.85 |
| 4,475,410 A | | 10/1984 | Jaeger |
| 4,537,071 A | * | 8/1985 | Waterman ................ 73/863.85 |
| 4,628,732 A | | 12/1986 | Makinen |
| 4,744,255 A | | 5/1988 | Jaeger |
| 5,747,708 A | | 5/1998 | Weiberth |
| 5,905,213 A | | 5/1999 | Jaeger |
| 6,467,500 B2 | * | 10/2002 | Fridlyand ................... 137/385 |
| 2002/0166392 A1 | * | 11/2002 | Handel |

* cited by examiner

Primary Examiner—Helen Kwok
Assistant Examiner—Nashmiya Fayyaz
(74) Attorney, Agent, or Firm—Pyle & Piontek (57) ABSTRACT

A sampling apparatus is characterized by a sampler operable to obtain samples of liquid product from a body of product in a vessel. The sampler includes a plunger having a sample receiving recess and a connecting device couples the sampler to the vessel at an aperture to the vessel. The sampler is attached to the connecting device and the connecting device is moveable between a first position placing the sampler into, and a second position taking the sampler out of, communication with the aperture. With the connecting device in the first position, the plunger is reciprocated to extend the plunger and its recess through the connecting device and vessel aperture into product in the vessel to receive a product sample in the recess. The plunger is then retracted from the vessel and through the connecting device to deliver the product sample to a collection point. During reciprocation of the plunger, a liquid seal is maintained between the vessel interior and sample collection point, and when the connecting device is moved to the second position, the sampler can be detached from the connecting device for service or repair, without escape of liquid from the vessel through the connecting device. Advantageously, the sampler remains stationary during movement of the connecting device between the first and second positions, so that additional space in which to accommodate movement of the sampler is not required when attaching the sampler and connecting device to the vessel.

14 Claims, 5 Drawing Sheets

LIQUID SAMPLER HAVING AN IN-LINE VALVE

BACKGROUND OF THE INVENTION

The present invention relates to apparatus for extracting samples of liquid from flow lines or vessels.

Certain manufacturing operations require that the immediate or overall composition of a liquid product flowing through a pipe or contained within a vessel or tank be monitored. Such monitoring may be accomplished using a sampling apparatus to take samples of product from a main body of the product. Where a composite sample of the product is required, the sampler is operated periodically to withdraw a series of small, measured amounts of the product at a sampling point, which individual samples are collected and mixed to form a composite sample representative of the total volume of product. If the immediate composition of the product is to be determined, individual samples are not collected and mixed, but are analyzed separately.

Four exemplary types of sampling apparatus of a type contemplated by the prior art are disclosed in U.S. Pat. Nos. 4,147,062, 4,262,553, 4,475,410 and 4,744,255, issued to Ben E. Jaeger, the present inventor, and the teachings of all of which are incorporated herein by reference. Sampling apparatus of the type disclosed in said patents is attached to an access line to a pipe or vessel containing liquid product. The samplers have a plunger that can be extended through the access line to project a sample receiving recess in the plunger into the main body of product in the pipe or vessel for receiving a product sample in the recess. The plunger is then retracted to move and deliver the product sample in the recess to a collection point in the sampler.

A disadvantage of the samplers of said patents is that they are always directly coupled through the access line with the interior of the pipe or vessel. The samplers therefore cannot be disconnected from the access line for replacement, repair or maintenance without first interrupting the presence of product in the pipe or vessel in the vicinity of the access line, since otherwise removal of the sampler from the access line would result in an uncontrolled outflow of liquid product through the access line.

U.S. Pat. No. 4,628,732, issued Dec. 16, 1986 and the teachings of which are incorporated herein by reference, teaches a connecting device for coupling a passive measuring instrument to a process having a parameter to be measured. The parameter may comprise temperature, density, pH value, consistency or some other characteristic of the process. The connecting device has a valve member through which a bore extends, and the valve member is movable between positions placing the bore into and taking the bore out of communication with the process. The measuring instrument connects to and is received within the valve bore. When the valve is positioned to place the bore into communication with the process, the measuring instrument can be extended through the bore and into the process to measure the parameter of the process. To replace or repair the measuring instrument, it is retracted from the process and the valve is moved to the position taking its bore out of communication with the process. The measuring instrument can then be disconnected from the valve member and removed from the valve bore without escape of process through and out of the bore. However, while the apparatus of said U.S. Pat. No. 4,628,732 permits a parameter of a process to be measured, it does not accommodate removal of a sample of the process.

U.S. Pat. No. 5,905,213, issued May 18, 1999 to the present inventor and the teachings of which are incorporated herein by reference, overcomes the aforementioned disadvantages of prior art samplers. According to this patent, principal components of a sampler for a liquid product can be disconnected from communication with an access line to the product without resulting in an uncontrolled outflow of liquid product through the access line. A forward end of a sampler housing is coupled to a movable valve for movement with the valve, and the housing and valve have axially aligned bores. Movement of the valve places the forward end of its bore into and out of communication with an opening in the access line leading to the interior of a vessel containing the liquid product. A plunger in the housing bore has a sample receiving recess intermediate its ends, and with the forward end of the valve bore placed into communication with the interior of the vessel, the plunger is reciprocated forward in the housing and valve bores to project the recess into the vessel to receive a product sample therein. The plunger is then reciprocated rearward to retract the product sample containing recess from the vessel and through the valve and housing bores to a sample collection point in the housing. Should the sampler require repair or replacement, the valve is moved to place the forward end of the valve bore out of communication with the vessel interior, whereupon the sampler housing can be disconnected from the valve without outflow of liquid product from the vessel through the valve bore. A disadvantage of the arrangement is that the entirety of the sampler moves conjointly with movement of the valve between its open and closed positions, so a relatively large unobstructed area must be provided around the sampler to accommodate such movement, which limits freedom of location of the sampling apparatus. In addition, to accommodate mounting of the sampler housing on the valve, the valve must be relatively large to accommodate connection of the sampler housing to it, resulting in increased manufacturing costs.

OBJECTS OF THE INVENTION

An object of the present invention is to provide a liquid sampler that can be removed from connection with a pipe or vessel carrying a liquid product to be sampled, without disturbing the product in the pipe or vessel.

Another object is to provide such a sampler that includes a valve that can be opened to place principal components of the sampler into communication with product in the line to permit the sampler to obtain one or more discrete samples of the product from the line.

A further object is to provide such a sampler in which the valve can be closed to place principal components of the sampler out of communication with product in the line to permit the components to be removed for service, repair or replacement without disturbing the product in the line or resulting in an uncontrolled outflow of product from the line.

Yet another object is to provide such a sampler in which the valve, when placing the sampler principal components into communication with the product in the line, accommodates extension of a sampling recess in a sampler plunger through a bore in the valve and into the product for receiving in the recess a product sample of measured volume for removal to a remote sampling point.

SUMMARY OF THE INVENTION

In accordance with the present invention, a sampling apparatus comprises a sampler that is operable to obtain discrete samples of liquid from a body of liquid in a vessel, and a connecting device for coupling the sampler to the vessel at an aperture to the vessel. The sampler is attached to the connecting device, and the connecting device is operable between a first position placing the sampler into communication with the liquid in the vessel through the aperture, and a second position taking the liquid sampler out of communication with the aperture and the liquid in the vessel. When the connecting device is in the second position, the sampler can be detached from the connecting device for service or replacement without liquid escaping from the vessel through the connecting device. The sampler includes sampling means that is extended, when the connecting device is in the first position, through the connecting device and into the vessel through the aperture to obtain a sample of liquid from the vessel, and that is then retracted from the vessel through the aperture and the connecting device to carry the liquid sample to a sample collection point. So that only liquid samples reach the collection point, seal means are provided to maintain a liquid seal between the liquid in the vessel and the sample collection point while the connecting device is in the first position. The sampler remains stationary when the connecting device is operated between the first and second positions, so that additional space to accommodate movement of the sampler need not be provided around the sampler and connecting device when the same are coupled to the vessel.

In a contemplated embodiment, the sampler includes a plunger having a sample receiving recess, and means are provided for reciprocating the plunger. When the connecting device is moved to the first position, the reciprocating means extends the plunger and its recess through the connecting device and the aperture into the liquid in the vessel to receive in the recess a sample of liquid. The reciprocating means then retracts the plunger and its recess from the vessel and through the aperture and the connecting device to deliver the liquid sample in the recess to the sample collection point. The connecting device includes a valve member having a bore, and the valve member is movable between the first and second positions. The valve member bore extends between the sampler and the aperture to the vessel when the valve member is moved to the first position, for reciprocation of the sampler plunger and its recess through the bore. The valve member bore is out of communication with each of the sampler and the aperture when the valve member is moved to the second position, whereupon the sampler can then be removed from the connecting device without escape of liquid from the vessel through the connecting device.

The means for maintaining a seal between the vessel interior and the sample collection point includes seal means carried by the plunger on opposite sides of the plunger recess, and the connecting device has a shell. The connecting device valve member comprises a ball valve contained within the shell, and the valve member bore extends generally diametrically through the ball valve. Means are provided for rotating the ball valve in the shell between the first and second positions, and the connecting device includes seal means in the shell for maintaining a seal between the ball valve bore and each of the vessel aperture and the sampler when the ball valve is rotated to the second position. The sampler includes a body, the plunger is received and reciprocated in the body, and the sampler body is attached to the connecting device shell.

The means for reciprocating the sampler plunger may include motor means, such as pneumatic motor means, coupled to the sampler plunger and attached to the sampler body opposite from attachment of the sampler body to the connecting device shell. The sampler plunger and the ball valve bore are generally cylindrical and are in a substantially coaxial orientation when the ball valve is rotated to the first position, so that reciprocation of the plunger through the valve member bore is unobstructed. When the ball valve is rotated to the second position, the axes of the plunger and bore are generally perpendicular.

The sampler body has a bore in which the plunger is received, and the sampler body bore is in substantial axial alignment with the ball valve bore when the ball valve is rotated to the first position. The sample collection point is in the sampler body bore, and the plunger is retracted into the sampler body bore to move its recess and the liquid sample in the recess to the sample collection point. Means are provided in the sampler body at the sample collection point for receiving the liquid sample from the plunger recess. Also included is means for releasably locking the connecting device ball valve in each of the first and second positions.

The foregoing and other objects, advantages and features of the invention will become apparent upon a consideration of the following detailed description, when taken in conjunction with the accompanying drawings.

DETAILED DESCRIPTION

The sampling apparatus of the invention is advantageous for use in applications requiring the capability to remove the sampler from a process line or vessel to which it is connected, for service, repair or replacement of the sampler, without need to first shut down the process line or interrupt the process in the line. This is accomplished by incorporating an isolation ball valve into the sampler assembly for selectively isolating the sampler from the process in the line. During normal operation, the ball valve is open and a plunger of the sampler is extended through a bore in the valve to project a sample chamber in the plunger into the process in the line to receive a sample of process in the sample chamber. The plunger is then retracted from the process and through the valve bore to deliver the sample in the sample chamber to a collection point in the sampler. The sampler includes means for accurately aligning of the valve bore with respect to the plunger to prevent interference with movement of the plunger through the bore. To remove the sampler for service, the plunger is retracted from the ball valve bore and the ball valve is closed to isolate principal components of the sampler from the process in the line. Principal components of the sampler can then be removed from the valve without resulting in an uncontrolled outflow of process through the valve.

Referring to the drawings, a sampling apparatus 20 embodying the teachings of the invention includes a liquid product or process sampler, motor means for operating the sampler, and a connecting device, respectively indicated generally at 22, 24 and 26. A bore or passage 28 extends through the connecting device 26 and the connecting device is actuable to selectively place the sampler 22 either into, or to take the sampler out of, communication with a main body of liquid product or process contained within a pipe or vessel 30. When the connecting device is actuated to place the sampler into communication with the vessel interior, the sampler may be operated by the motor means 24 to obtain discrete product samples of measured volume from the main body of product and to convey the samples to a collection point. When the connecting device is actuated to take the sampler out of communication with the vessel interior, a principal portion of the sampling apparatus, i.e., the sampler 22 and motor means 24, can be detached and removed from the connecting device 26 for maintenance, repair or replacement, without occurrence of an uncontrolled outflow of product from the vessel. The invention advantageously enables the sampler 22 and motor means 24 to be removed for service or replacement without the need to first interrupt the flow or presence of product in the vessel in the vicinity of the sampling apparatus.

The sampler 22 includes a plunger assembly, indicated generally at 32. The plunger assembly has a sample-receiving portion comprising an opening, annular recess or sample chamber 34 formed in the plunger assembly. The sample-receiving portion can be extended, with forward reciprocation of the plunger assembly by the motor means 24, through the connecting device 26 and into the vessel 30 to receive a sample of liquid product. The sample-receiving portion is then retracted from the vessel, with rearward reciprocation of the plunger assembly by the motor means, to convey the product sample through the connecting device and to a delivery point in the sampler for collection, for example in a container 36 supported by an outlet adapter 37. The sample-receiving portion, which in the illustrated embodiment of sampling apparatus is an annular recess, may be sized to receive and contain a precise volume of the product, and the sampler may be periodically operated so that the collected product samples represent a composite sample of the product in the vessel. The motor means 24 for operating the sampler 22 may comprise a pneumatic motor means, as shown, or any other suitable motor means, such as an electric motor or a handle accommodating manual reciprocation of the plunger assembly. During reciprocation of the plunger assembly 32, seals carried by the plunger assembly always maintain a liquid seal between the interior of the vessel and the sample collection point and between the sample collection point and the motor means, so that the sampling apparatus is generally insensitive to the pressure of the liquid in the vessel and the collected sample is protected against contamination.

The sampler 22 has a head 38 connected to a forward end of a sampler body 40 by fasteners 42 with respective cylindrical passages or bores 44 and 46 in the body and head in axial alignment. A rearward end of a shell 48 of the connecting device 26 is received in a circumferential stepped recess in a forward end of the head 38. The shell is connected to the head by fasteners 50 and sealed to the head by a seal 51. The connecting device comprises a valve assembly having a ball valve 52 contained for rotation within the shell. The valve assembly cylindrical passage 28 extends diametrically through the ball valve and the ball valve may be rotated between a valve-open position where the valve passage is axially aligned with the head and body passages 44 and 46, and a valve-closed position where the axis of the valve passage is generally perpendicular to the axes of the head and body passages. At opposite ends of the passage 28 the ball valve has flat surfaces 53A and 53B lying in parallel planes that are perpendicular to the axis of the passage. A flushing fluid inlet port 54 and a product sample outlet port 56 in the body 40 intercept the body bore 46 at a sample collection point in the sampler.

The motor means 24 may comprise a pneumatic motor means having a cylinder 58 closed at a rearward end, connected at a forward end to a rearward end of the body 40 by a quick release clamp 60 and sealed to the body by a seal 62. The cylinder has a bore 64 axially aligned with the bores 28, 44 and 46, and within the bore 64 is a cylinder rod 66 having an integral piston 68 sealed to the cylinder bore by seals 69. The piston and piston rod are driven or reciprocated in a forward or rightward direction by introduction of air under pressure to an air inlet 70 in the rearward or left end of the cylinder bore, and are driven in a rearward or leftward direction by introduction of air under pressure to an air inlet 72 formed in the body 40 and leading to the right end of the cylinder bore. The cylinder rod 66 extends forward through a pair of seals 74 carried in a rearward end of the sampler body 40 on opposite sides of a drain vent 75 that leads to the exterior of the body. The drain vent allows escape of any fluid that might leak past the seals 74, so that fluid from the sampler 22 does not enter the motor means 24 and, conversely, so that fluid from the motor means does not enter the sampler.

When the valve assembly 26 is open, the plunger assembly 32 reciprocates within the body, head and ball valve bores 46, 44 and 28, as well as within a pair of bushings 78 and 80. The bushing 78 is press fit into the rearward end of the head bore 44 and extends outward and rearward from the head bore into the body bore 46, and a seal 82 seals the connection between the body, head and bushing. The bushing 80 is press fit into a forward end of a passage 84 through the valve assembly shell 48.

The plunger assembly 32 includes a plunger 86 in which is formed an annular recess or sample receiving chamber 34 that advantageously is of selected volume. The plunger carries three seals 90 forward from the sample chamber and three seals 92 rearward from the sample chamber. A wrench socket 94 is provided in the front face of the plunger and a forward end of the motor means piston rod 66 is threaded to a rearward end of the plunger. Actuation of the motor means 24 reciprocates the plunger assembly 32 within the bushings 78 and 80 and the ball valve passage 28, and reciprocates the piston rod 66 within the body passage 46. The plunger assembly and piston rod are of smaller diameters than the diameters of the passages within which they reciprocate. In consequence, the seals 90 and 92 carried by the plunger assembly, the seals 74 through which the piston rod extends, and the piston seals 69, control the concentricity of the plunger assembly and piston rod within the passages and function as bearings to enable them to reciprocate easily. This prevents direct sliding contact between the relatively hard components of the sampler, whereby the life of the sampler is extended and its repair frequency is reduced. In operation of the sampling apparatus and during reciprocation of the plunger assembly, the seals 90 and 92 continuously maintain a seal between the outlet port 56 and the product in the pipe 30, and wipe the bores clean of sampled product with reciprocation of the plunger assembly.

The sampling apparatus 20 is coupled to the pipe or vessel 30 by an adapter 96 that is welded at 98 to the pipe around the periphery of an opening 100 to the pipe. A forward end of the valve assembly shell 48 has a reduced diameter and is extended into the rearward end of a passage 99 through the adapter, and a seal 101 seals the adapter and shell. The head 38, shell 48 and adapter 96 are connected by the plurality of fasteners 50. Fasteners 104 also serve to hold the shell and head together, so that the ball valve 52 does not accidentally fall out from between the shell and head when they are connected to and disconnected from the adapter.

With the ball valve 52 in the open position, its bore 28 is axially aligned with the longitudinal axis of the plunger assembly 32. The motor means 24 can then be actuated by application of compressed air at the inlet 70, to extend the plunger assembly forward and move its sample-receiving chamber 34 into the liquid product in the pipe 30. During forward extension of the plunger assembly, the rearward plunger seals 92 form a seal within the bushing 78, just forward from the outlet port 56, before the forward plunger seals 90 move out of the bushing 80 and into the pipe. During leftward retraction of the plunger assembly, the forward plunger seals 90 enter the bushing 80 before the rearward plunger seals 92 move out of the bushing 78 and expose the ports 54 and 56. In this manner, a seal is at all times maintained between product in the pipe and the sampler outlet port, so that only the product sample received and contained in the sample chamber 34 reaches the outlet port.

Upon extending the plunger assembly 32 forward to obtain a product sample, the sample chamber 34 is projected into the pipe 30 and exposed to the stream of product. The sample chamber is therefore washed by the product stream upon each cycle of operation of the sampler. This prevents an accumulation of "stale" product in the chamber, while the annular shape of the chamber and its direct exposure to the product stream help prevent it from becoming clogged by any solids as may be in the product. The sample-receiving chamber is therefore self-cleaning of debris that may be encountered in product lines, so that when the sample chamber is retracted from the pipe, it carries a true and uncontaminated sample of the product to the sample collection point at the outlet port 56.

After a product sample is collected in the sample chamber 34 of the plunger assembly 32, the motor means 24 is operated by application of air under pressure to the air inlet 72 to fully retract the plunger assembly into the sampling apparatus 20. With full retraction of the plunger assembly, the sample chamber 34 is moved rearward to the sample collection point at the outlet port 56 for delivery of the product sample from the sample chamber into and through the outlet port for collection. To facilitate removal of the product sample from the sample chamber if and as necessary, a suitable fluid may be introduced through the inlet port 54 to flush or blow the sample from the sample chamber. Alternatively or simultaneously, vacuum may be applied to the outlet port. This enables substantially any type of liquid product to readily be ejected from the sample chamber.

Figure 1:
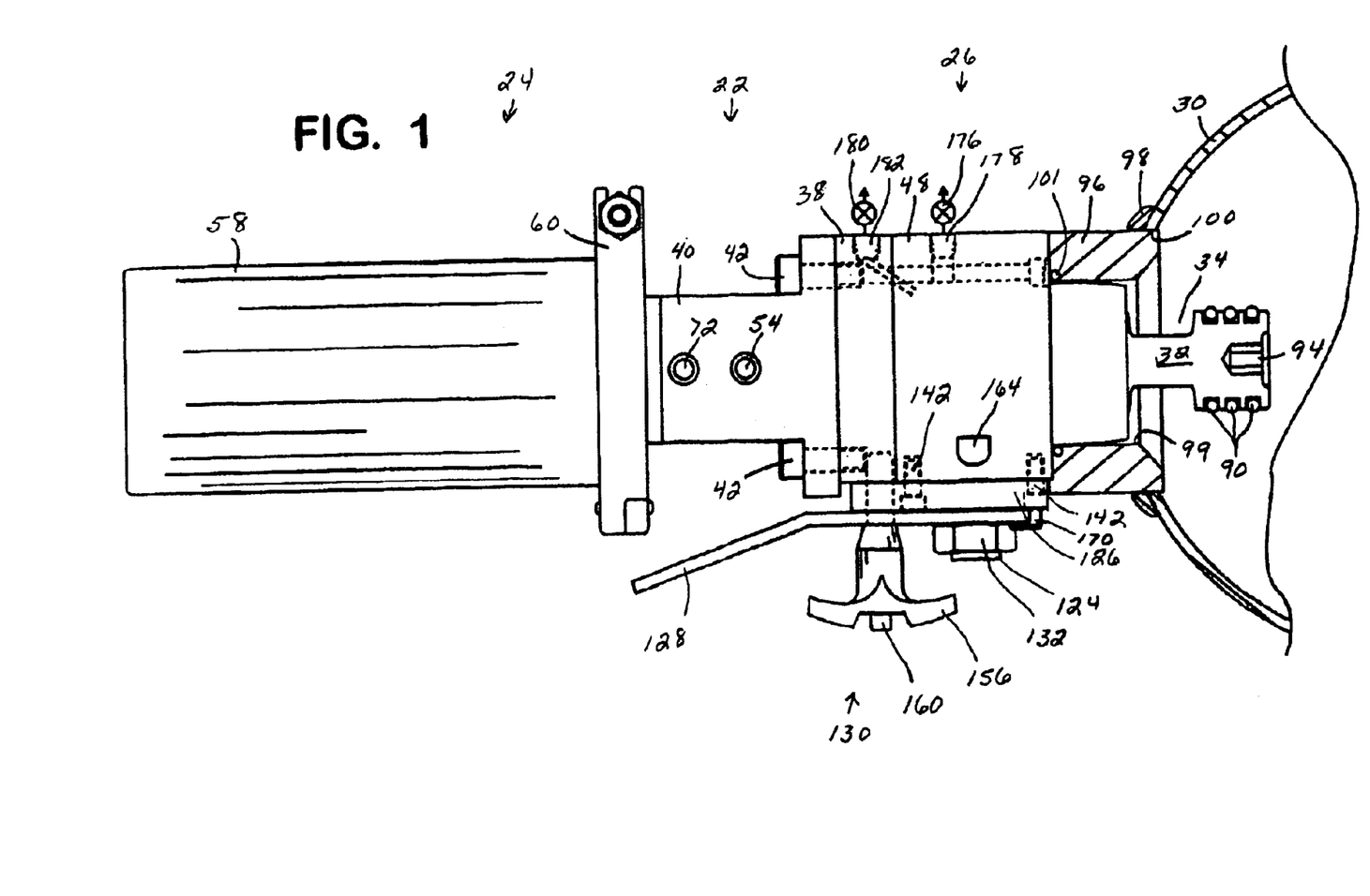
FIG. 1 is a top plan view of a sampler embodying the teachings of the present invention.
Figure 2A:
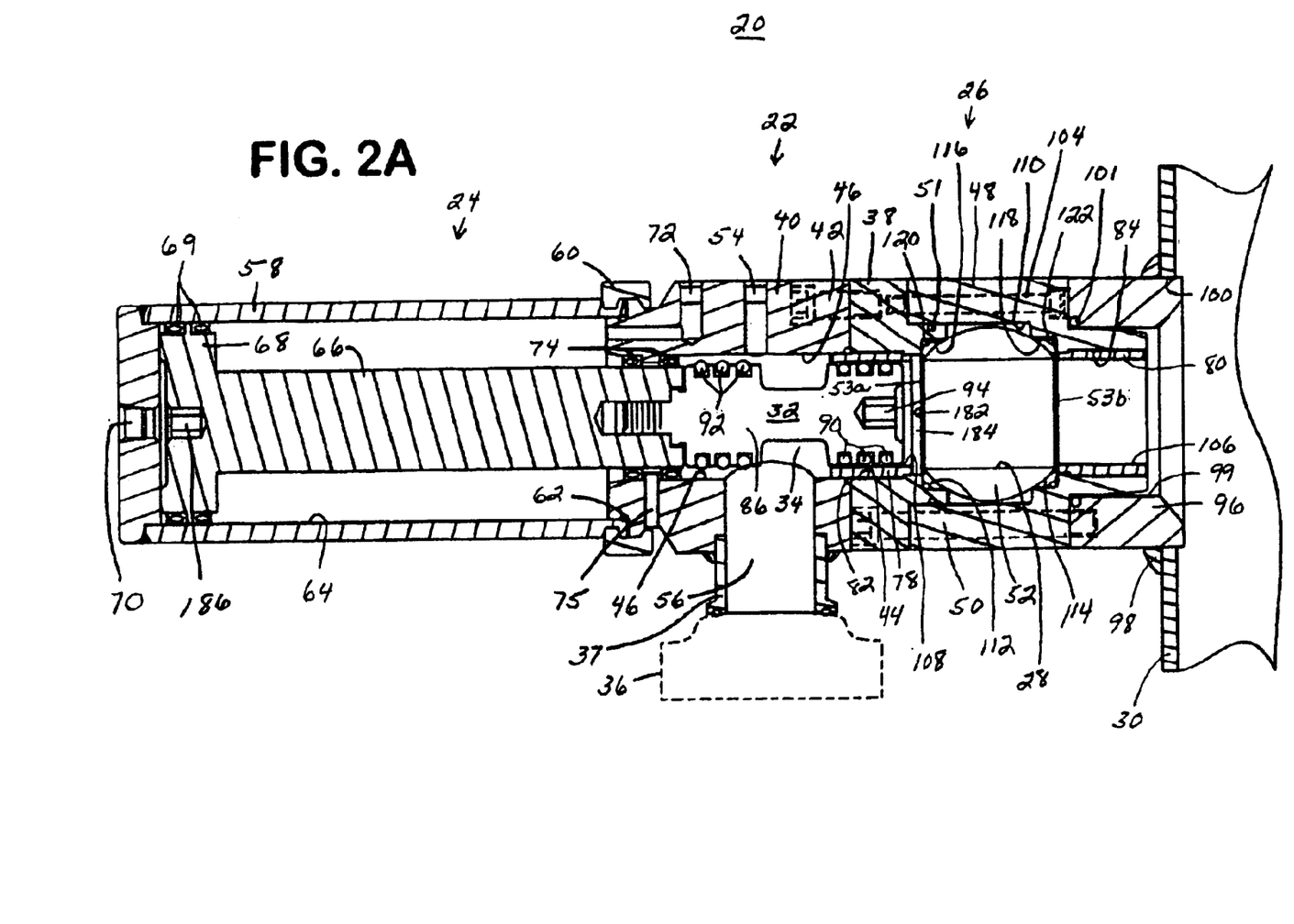
FIG. 2A is a cross sectional side elevation view of the sampler, showing the sampler in its sample delivering position.
Figure 2B:
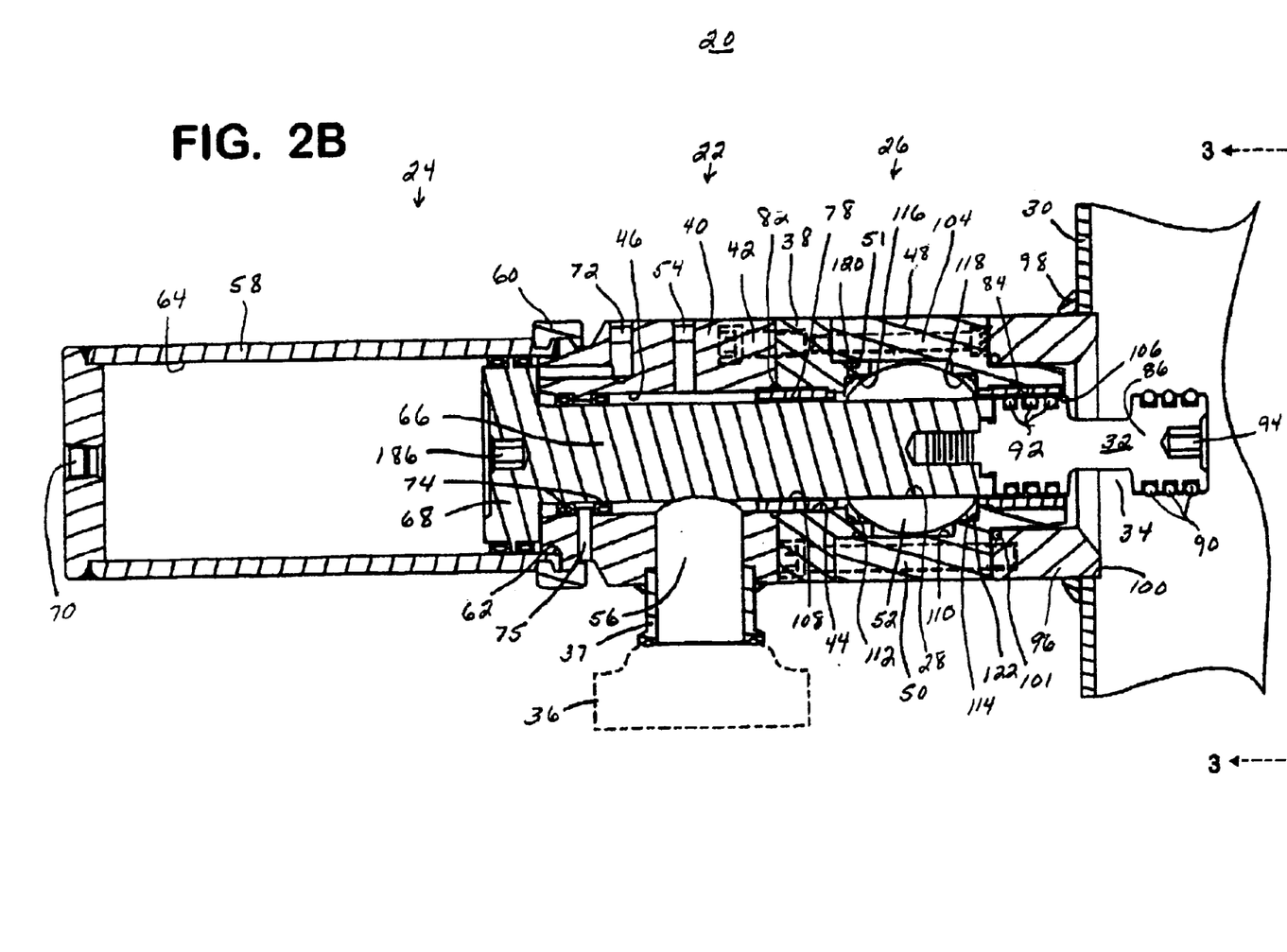
FIG. 2B is similar to FIG. 2A, except that the sampler is in its sample receiving position.

In FIGS. 2A and 2B, the ball valve 52 of the valve assembly 26 is shown rotated to its open position, such that the passage 28 through the ball valve is coaxial with bushing passages 106 and 108 through the bushings 80 and 78, as well as with the longitudinal axis of the plunger assembly 32. Consequently, when the plunger assembly is extended forward by the motor means 24, the forward end of the plunger assembly and its sample chamber 34 are projected into the pipe 30 to receive a product sample in the sample chamber. Rearward retraction of the plunger assembly by the motor means then moves the plunger assembly and the sample chamber with the product sample therein into the sampling apparatus and delivers the product sample to the collection point between the inlet and outlet ports 54 and 56. During reciprocation of the plunger assembly, the plunger seals 90 and 92 at all times maintain a seal between the pipe interior and the collection point.

The invention contemplates rotation of the valve assembly 26 to its closed position, such that the passage 28 through the ball valve 52 is out of communication with and sealed from the bores 106 and 108 through the bushings 80 and 78, and therefore out of communication with product in the pipe 30. When the ball valve is closed, the sampler 22 and motor means 24, which together comprise principal components of the sampling apparatus 20, can be disconnected and removed from the valve assembly for service, repair and/or replacement, without occurrence of an uncontrolled outflow of liquid product from the pipe. The invention therefore advantageously enables principal components of the sampling apparatus to be removed for service or replacement without need to interrupt product flow through the pipe.

The ball valve 52 of the valve assembly 26 is received in a cylindrical passage 110 in the shell 48 and confined therein between a shoulder at a forward end of the head 38 and a shoulder at a forward end of the shell passage 110. The ball valve is supported for rotation and sealed to the head and shell by filled Teflon® annular seals 112 and 114 that are received in respective annular recesses 116 and 118 at forward ends of the head passage 44 and shell passage 110. O-ring seals 120 and 122 are in the recesses behind and provide resilience to respective Teflon® seals 112 and 114, which by virtue of being filled are resistant to abrasion, but are also relatively stiff. The O-rings accommodate some movement of the Teflon® seals, since when the ball valve is closed it is pressurized on its forward side and urged rearward by the pressure of product in the line 30. When such rearward movement of the ball valve occurs, the filled Teflon® seal 112 is moved rearward by the ball valve, with the resilience of the O-ring 120 then accommodating movement and some compression of the seal 112 without damage. Excessive rearward movement of the ball valve and crushing of the seal 112 is prevented by engagement of the ball valve with a shoulder at the forward end of the head passage.

When the ball valve 52 is rotated to the open position, the axis of the passage 28 through the ball valve must be coaxially aligned with the longitudinal axis of the plunger assembly 32 to allow the plunger assembly to be reciprocated through the ball valve passage without interference. This is accomplished with a ball valve opening/closing mechanism comprising a stem 124, a cam 126, a handle 128, a lock-pin assembly indicated generally at 130, and a nut 132. The stem 124 extends through a passage 134 in the valve assembly shell 48 and is sealed with the shell by a seal 136. A longitudinal axis of the stem is perpendicular to the axis of the ball valve passage 28 and an inner end of the stem is coupled to the ball valve by a spline comprising a flat key 138 at the inner end of the stem that fits with close tolerance into a groove 140 in the ball valve. The cam 126 is attached to the shell 48 by a plurality of fasteners 142 and the stem extends outward through a passage 144 in the cam. Outward from the cam, the stem is coupled to the handle 128 by a spline connection comprising a flat key 146 portion of the stem that fits with close tolerance into a slot 148 in the handle. The nut 132 threads onto the outermost end of the stem to attach the handle to the stem. Because of the close tolerance of the spline connections at opposite ends of the stem to each of the handle and ball valve, rotation of the handle precisely conjointly rotates the ball valve When the ball valve 52 is rotated to its open position, means are provided to ensure that it is in, and to lock it in place in, proper rotational orientation with respect to the plunger assembly 32. The ball valve also is locked in place when it is rotated to its closed position, so that it will not be accidentally opened. For the purpose, a passage 150 is in the handle 128 and two passages 152 and 154 are in the cam 126. When the handle and ball valve 52 are rotated to the position where the handle passage 150 and cam passage 152 are coaxial, the ball valve is in its open position and the ball valve passage 28 is coaxial with the axis of the plunger assembly 32, so that the plunger assembly can be reciprocated through the ball valve passage without interference. When the handle and ball valve are rotated to the position where the handle passage 150 and the cam passage 154 are coaxial, the ball valve is in its closed position and the axis of the ball valve bore is generally perpendicular to the axes of the plunger assembly and the passage 106 through the bushing 80.

Figure 3:
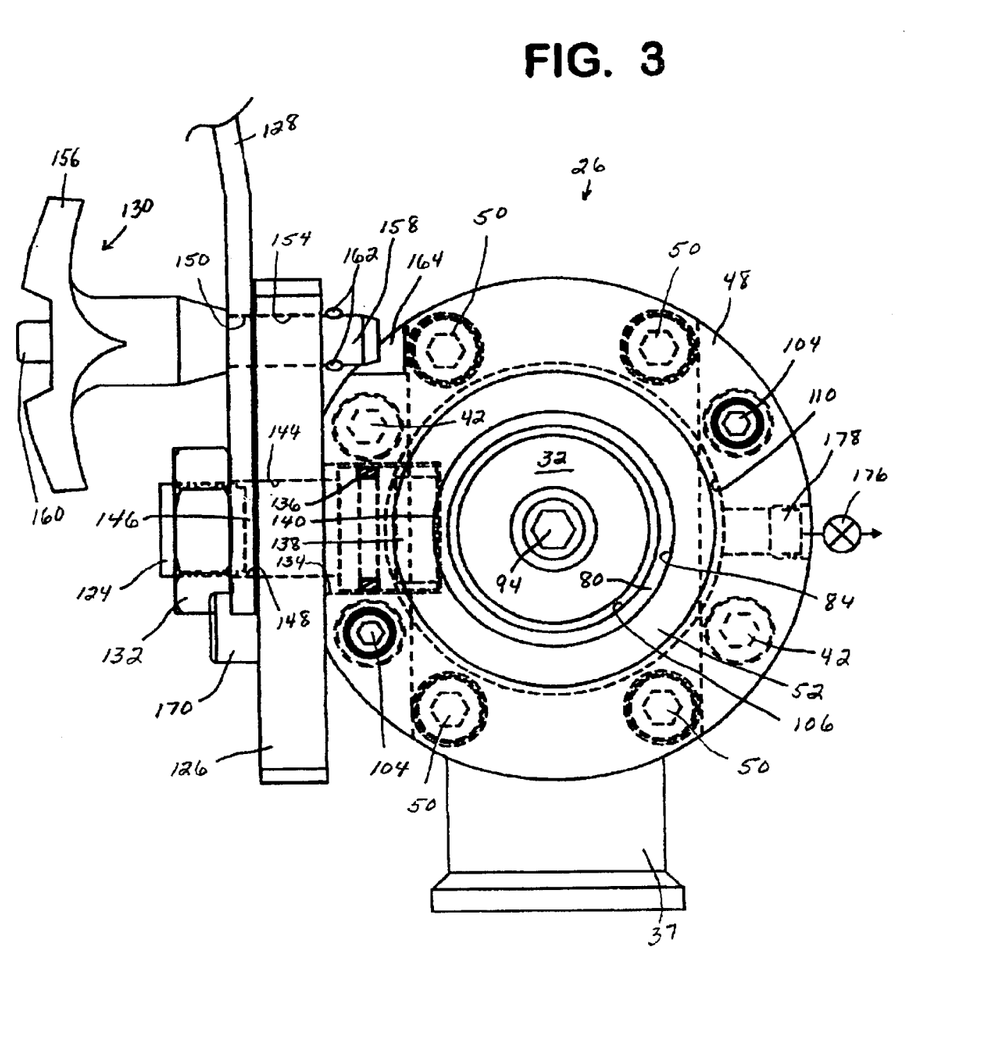
FIG. 3 is a view taken substantially along the lines 3—3 of FIG. 2B, except that the product carrying pipe and adapter for connecting the sampler to the pipe are not shown.

The lock-pin assembly 130 is used to precisely orient and lock the handle 128 and ball valve 52 in each of the valve open and closed positions. The lock-pin assembly includes a handle 156 and a cylindrical stem 158 extending forward from the handle. A plunger 160 extends through the stem and rearward out of the handle, and two diametrically opposed balls 162 extend partially out of a forward end of the stem. The plunger is spring loaded outward from the handle and operates in a well known manner to hold the balls 162 in a position extending partially outward from the surface of the stem (as shown in FIG. 3) when the plunger is not pressed into the handle, and to release the balls for movement into the stem when the plunger is pressed into the handle. The handle and cam passages 150, 152 and 154 are of a diameter just slightly greater than that of the cylindrical stem 158 for a close fit of the stem in the passages.

When the handle 128 is rotated to close of the ball valve 52, the handle and cam passages 150 and 154 are, or are close to being, coaxial. The lock-pin assembly 130 is then used to precisely orient and lock the handle and ball valve in position. This is accomplished by extending the lock-pin assembly stem 158 through the passages 150 and 154 while depressing the plunger 160 to release the balls 162 for movement radially inward of the stem and while simultaneously moving the handle, if necessary, to accurately coaxially align the passages, so that the stem can be extended through both of the passages. When the stem is fully extended through the passages, the plunger 160 is released to hold the balls 162 in their radially outward positions and lock the stem against accidental retraction from the passages. At this time, a recess 164 in the shell 48 accommodates the forward end of the stem.

When the handle 128 is rotated to open the ball valve 52, the handle and cam passages 150 and 152 are, or are close to being, coaxial. The lock-pin assembly 130 is then again used to precisely orient and lock the handle and ball valve in position. This is accomplished by extending the lock-pin assembly stem 158 through the passages 150 and 152 while depressing the plunger 160 to release the balls 162 for movement radially inward of the stem and while simultaneously moving the handle, if necessary, to accurately coaxially align the passages, so that the stem can be fully extended through both of the passages. The plunger is then released to hold the balls 162 in their radially outward positions and lock the stem against accidental retraction from the passages. At this time, a recess (not shown) in the head 38 accommodates the forward end of the stem. To prevent the lock-pin assembly from being lost or misplaced, it is attached to one end of a cable 166, an opposite end of which may be attached to the sampling apparatus, such as to a bolt 168.

Figure 4A:
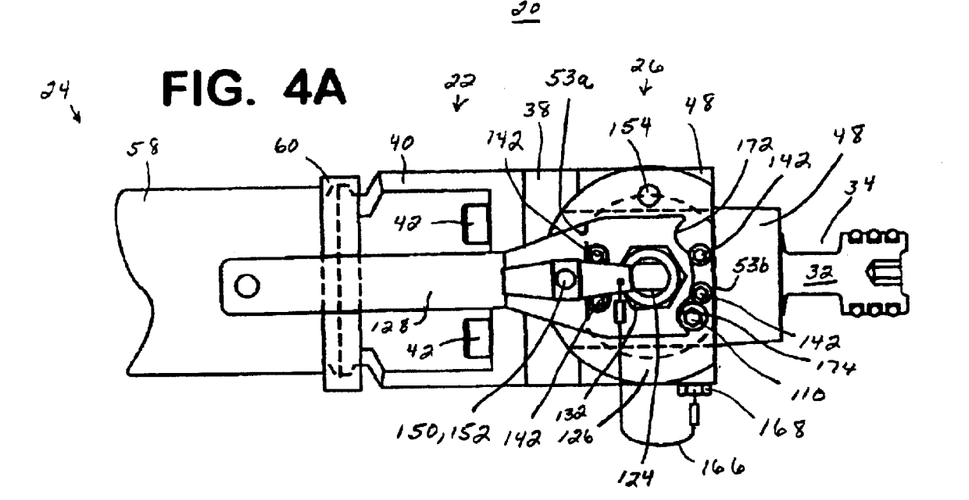
FIG. 4A is a partial side elevation view of the sampler, showing a valve control handle of the sampler in a valve open position.
Figure 4B:
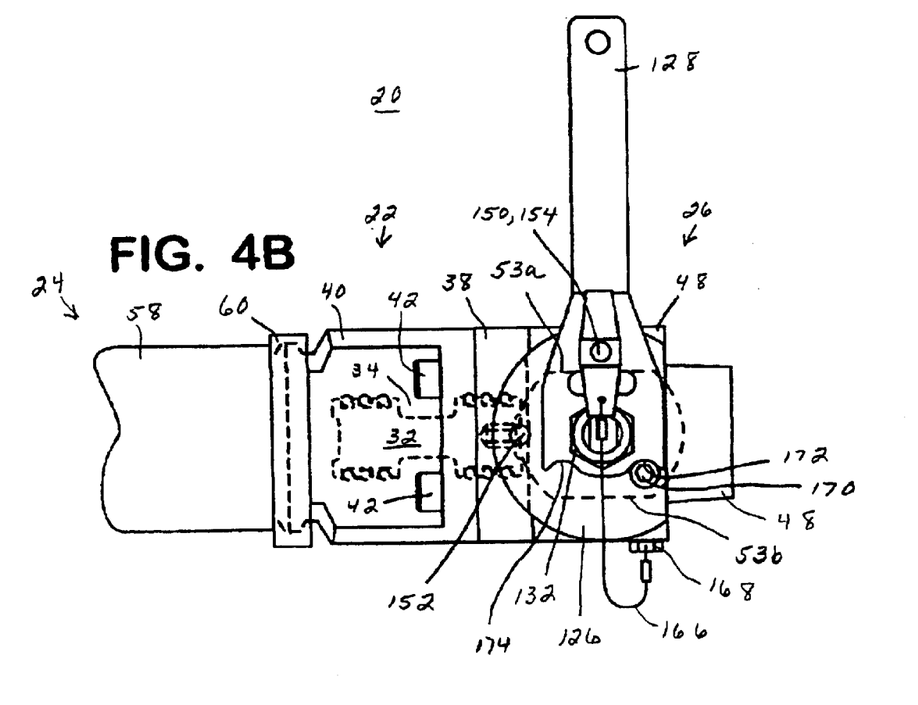
FIG. 4B is a partial side elevation view of the sampler, showing the valve control handle in a valve closed position.

To facilitate placement of the handle 128 at the open and closed positions of the ball valve 52, the cam 126 has a stop 170 and the handle has first and second stop-engaging indentations 172 and 174. As seen in FIG. 4A, when the handle is rotated counterclockwise to open the ball valve, it is rotated to the point where further rotation is blocked by engagement of the handle indentation 174 with the stop 170, at which point the handle and cam passages 150 and 152 are, or are close to being, coaxially aligned. Insertion of the lock-pin assembly stem 158 into the passages 150 and 152 then brings the passages into precise coaxial alignment and locks the handle and ball valve in the valve open position, with the axis of the ball valve passage 28 then being coaxial with the longitudinal axis of the plunger assembly 32. As seen in FIG. 4AB, when the handle is rotated clockwise to close the ball valve, it is rotated to the point where further rotation is blocked by engagement of the handle indentation 172 with the stop 170, at which point the handle and cam passages 150 and 154 are, or are close to being, coaxially aligned. Insertion of the lock-pin assembly stem 158 into the passages 150 and 154 then brings the passages into precise coaxial alignment and locks the handle and ball valve in the valve closed position, with the axis of the ball valve passage 28 then being generally perpendicular to the longitudinal axis of the plunger assembly and the axis of the forward bushing passage 106. The stop therefore serves to facilitate positioning the handle and ball valve in the open and closed positions of the valve, while the lock-pin assembly brings the handle and ball valve precisely to, and locks the handle and ball valve in, the valve open and closed positions.

With the handle 128 and ball valve 52 locked in the valve open position, the motor means 24 is actuated to reciprocate the plunger assembly 32 in both directions through the ball valve passage 28 and into and out of the product in the pipe 30. As above described, successive liquid product samples from the pipe are then received in the sample chamber 34 and conveyed to the collection point in the sampler 22 for removal from the sample chamber and collection.

The invention contemplates that principal components of the sampling apparatus be disconnected and removed from the ball valve assembly 26 for repair, service or replacement, without need to interrupt the product in the line 30. Beginning with the ball valve assembly in the open position, this is accomplished by activating the motor means 24 to fully retract the plunger assembly 32, and then deactivating the motor means by shutting off supply of compressed air to its air inlets 70 and 72. The lock-pin assembly 130 is then removed from the handle and cam passages 150 and 152, the ball valve assembly 26 is closed by rotation of the handle 128 to the valve closed position, and the lock-pin assembly is inserted into the handle and cam passages 150 and 154 to lock the valve in the closed position. At this point, a test is made of the integrity of the valve assembly seal 112 to ensure that the seal is not leaking and that the sampler 22 and motor means 24 can be removed from the valve assembly 26 without occurrence of an uncontrolled outflow of product through the valve. This test is conducted by opening a valve 180 at an outlet port 182 that extends through the head 38 to an annular recess 184 in the head passage 46 forward from a forward end of the bushing 78 and rearward from the valve assembly seal 112. Opening the valve 180 also serves to relieve any pressure of product as may be in the head and body passages 44 and 46 in front of the plunger 32, so that the sampler does not contain pressurized product and can be safely detached and removed from the valve assembly. The valve assembly forward seal 114 can leak in the presence of sufficient pressure of product, so if there is no continuing outflow of product from the open valve 180, it is known that the rearward valve assembly seal 112 is good. The sampler and motor means can then be detached and removed from the valve assembly without occurrence of an uncontrolled outflow of product from the pipe 30 through the valve assembly.

With the valve assembly 26 remaining closed, the motor means 24 and sampler 22 (except for the head 38) are separated from the valve assembly by removing the fasteners 42. This permits the sampler body 40 to be pulled rearward away from the head 38, removing the forward end of the body passage 46 from around the pilot diameter of the rearward end of the bushing 78 and carrying the plunger assembly 32 and its seals 90 to the left and out of the bushing. At this point, a protective closure (not shown) may be placed over the rearward end of the head.

With the motor means 24 and sampler body 40 separated from the head 38 and valve assembly 26, air is applied to the motor means air inlet 70 to drive the plunger assembly 32 forward out of the sampler body passage 46. The sampler body is then separated from the motor means by removing the quick release clamp 60 attaching the motor means cylinder barrel 58 to the sampler body, and the cylinder barrel is pulled from around the integral piston rod 66 and piston 68. Wrenches are then used in the wrench socket 94 at the forward end of the plunger assembly 32 and in a wrench socket 186 at a rearward end of the piston to unscrew and separate the plunger assembly from the piston rod 66. Any worn components, such as worn plunger assembly seals 90 and 92, piston rod seals 74 and piston seals 69 can then be readily accessed and replaced.

It can happen that closure of the ball valve assembly 26 does not effectively seal product in the pipe 30 from the passage 44 in the head 38. If when the valve 180 is opened to test the integrity of the valve assembly seal 112, there occurs a continuing outflow of product from the valve, that indicates that at least the ball valve seal 112 is worn and requires replacement, in which case the seal 114 would also be replaced as preventive maintenance.

To replace the ball valve assembly Teflon® seals 112 and 114 requires removal of the ball valve assembly 26 from the adapter 96, in which case the presence of product in the line 30, at least in the vicinity of the sampling apparatus 20, must first be interrupted. With the process line shut down, for operator safety the apparatus is first depressurized by opening the valve 180 to relieve any pressure of product in the head passage 46 and by opening the valve 176 to relieve any pressure of product in the valve assembly. The sampler 22 and motor means 24 are then disconnected from the head 38 and ball valve assembly as above described, following which the lock-pin 130 is removed, the handle 128 is rotated to open the ball valve assembly and the fasteners 50 are removed to release the sampler head 38 and ball valve assembly shell 48 for removal from the adapter 96. When the sampler head and shell are separated from the adapter, fasteners 104, extending between the head and shell, continue to hold the head and shell together to prevent the ball valve 52 from accidentally falling out of the shell. Removal of the fasteners 104 then allows separation of the head and shell and removal of the ball valve 52 rearward from and out of the shell. This provides access to the Teflon® seals 112 and 114, to the O-rings 120 and 122, and to the bushings 78 and 80 for service or replacement.

Should the stem seal 136 require inspection or replacement, the cam fasteners 142 are removed to allow the handle 128, the cam 126 and the stem 124 to be separated from the shell 48 for access to the stem seal.

The sampling apparatus 20 is reassembled in the reverse order of disassembly. During reassembly, care is taken to ensure that when the ball valve assembly 26 is locked in the open position, the valve passage 28 is coaxially aligned with the longitudinal axis of the plunger assembly 32 for unobstructed reciprocation of the plunger assembly through the passage. This is accomplished by making the counterbores in the cam 126, which accommodate the heads of the cam fasteners 142, about 0.032" larger in diameter than the diameters of the heads of the fasteners to allow limited adjustment of the cam relative to the valve assembly shell 48 during attachment of the cam to the shell. During attachment of the cam to the shell, the fasteners 142 are not initially fully tightened. First, while the fasteners are slightly loose, the cam is moved to bring the ball valve passage 28 into axial alignment with the passages 106 and 108 through the bushings 80 and 78, and upon alignment, the fasteners are tightened. The ball valve passage is then axially aligned with the longitudinal axis of the plunger assembly.

To the extent that the sampling apparatus 20 of the present invention permits principal components of the sampler to be disassembled without interruption of process in a vessel to which the sampling apparatus is attached, it has some similarity to the sampling apparatus of aforementioned U.S. Pat. No. 5,905,213, issued to the present inventor. However, significant differences exist. In the sampling apparatus of said patent, a forward end of a sampler housing mounts to a valve and the entirety of the sampling apparatus, including the sampler housing and motor means, rotates with the valve when the valve is rotated between open and closed positions. On the other hand, in the sampling apparatus of the present invention the forward end of the sampler housing mounts to the ball valve housing, but the ball valve rotates within its housing without rotation of the housing itself, so that the sampler and its motor remain stationary while the valve is opened and closed. Consequently, since the sampler and its motor do not rotate and swing in an arc with opening and closing of the valve, an enlarged area providing sufficient room in which to mount the sampling apparatus is not required. In addition, unlike the sampler of said patent where the ball valve is exposed to the external environment, in the sampler of the invention the ball valve is contained within a housing and protected against external elements. Further, the ball valve of the invention can be of a relatively smaller size than might otherwise be necessary, since the sampler housing mounts not to the ball valve itself, but to a housing for the ball valve.

While embodiments of the invention have been described in detail, one skilled in the art can devise various modifications and other embodiments without departing from the spirit and scope of the invention, as defined in the accompanying claims.

What is claimed is:

1. A sampling apparatus, comprising:
a sampler operable to obtain discrete samples of liquid product from an interior of a vessel, said sampler including a plunger having a sample receiving recess;
a connecting device for coupling said sampler to the vessel, wherein said sampler is attached to said connecting device and said connecting device is movable between a first position placing said sampler into communication with the interior of the vessel and product therein and a second position taking said sampler out of communication with the interior of the vessel and product therein, said sampler being detachable from said connecting device, without escape of product from the vessel, when said connecting device is in said second position, means for reciprocating said sampler plunger, when said connecting device is in said first position, to extend said plunger and recess through said connecting device and into the product in the vessel interior to receive in said recess a predetermined volume sample of product, and to then retract said plunger and recess from the vessel interior and through said connecting device to deliver the predetermined volume product sample in said recess to a sample collection point in said sampler; and means for continuously maintaining a seal between the interior of the vessel and said sample collection point during reciprocation of said plunger, wherein said sampler remains stationary during movement of said connecting device between said first and second positions and said connecting device includes a valve member having a passage, said valve member being movable between said first and second positions and said valve member passage extending between said sampler and the vessel interior when said valve member is moved to said first position for reciprocation of said sampler plunger and recess through said passage into the product in the vessel interior, and said valve member passage being out of communication with said sampler and the vessel interior when said valve member is moved to said second position, said means for continuously maintaining a seal sealing said sampler plunger with said valve member passage upon reciprocation of said plunger through said passage, said connecting device including a shell, said connecting device valve member comprising a ball valve within said shell and said passage extending diametrically through said ball valve, and further including means for rotating said ball valve in said shell between said first and second positions, wherein said connecting device includes seal means in said shell for maintaining isolation between said ball valve passage, said sampler and the vessel interior when said ball valve is rotated to said second position, and wherein said sampler is attached to said connecting device shell, and including first valve means operable when said ball valve is rotated to said second position for venting any pressure of product within said shell and for checking the integrity of said seal means, and second valve means operable when said ball valve is rotated to said second position for venting any pressure of product within said sampler and for checking the integrity of said seal means.

2. A sampling apparatus as in claim 1, wherein said sampler includes a body having a passage, said plunger is reciprocated in said body passage, said seal means is sealable with said body passage upon reciprocation of said plunger through said body passage and said body is attached to said connecting device shell.

3. A sampling apparatus as in claim 2, wherein said means for reciprocating said sampler plunger includes motor means coupled to said sampler plunger and attached to said sampler body opposite from attachment of said sampler body to said connecting device shell.

4. A sampling apparatus as in claim 1, wherein said means for reciprocating said sampler plunger includes motor means.

5. A sampling apparatus as in claim 4, wherein said motor means includes pneumatic motor means.

6. A sampling apparatus as in claim 1, wherein said sampler plunger is cylindrical and said valve member passage is cylindrical and coaxial with said plunger when said valve member is moved to said first position for unobstructed reciprocation of said plunger through said passage.

7. A sampling apparatus as in claim 6, wherein said sampler plunger longitudinal axis and valve member passage axis are generally perpendicular when said valve member is moved to said second position.

8. A sampling apparatus as in claim 2, wherein said sampler body passage is in axial alignment with said valve member passage when said valve member is rotated to said first position, said sample collection point is at a point in said sampler body passage, and said plunger is retracted into said sampler body passage to move said recess and the liquid sample in said recess to said sample collection point.

9. A sampling apparatus as in claim 8, including means in said sampler body at said sample collection point for receiving the liquid sample from said plunger recess.

10. A sampling apparatus as in claim 1, including means for releasably locking said connecting device in each of said first and second positions.

11. A sampling apparatus as in claim 1, wherein said sampler plunger is generally cylindrical, said ball valve passage is generally cylindrical and coaxial with said plunger longitudinal axis when said ball valve is rotated to said first position for unobstructed reciprocation of said plunger through said ball valve passage, and including means for locking said ball valve in and unlocking said ball valve from each of said first and second positions.

12. A sampling apparatus, comprising:

a sampler operable to obtain discrete samples of liquid product from an interior of a vessel, said sampler including a plunger having a sample receiving recess;

a connecting device for coupling said sampler to the vessel, wherein said sampler is attached to said connecting device and said connecting device is movable between a first position placing said sampler into communication with the interior of the vessel and product therein and a second position taking said sampler out of communication with the interior of the vessel and product therein, said sampler being detachable from said connecting device, without escape of product from the vessel, when said connecting device is in said second position, means for reciprocating said sampler plunger, when said connecting device is in said first position, to extend said plunger and recess through said connecting device and into the product in the vessel interior to receive in said recess a sample of product, and to then retract said plunger and recess from the vessel interior and through said connecting device to deliver the product sample in said recess to a sample collection point; and means for maintaining a seal between the interior of the vessel and said sample collection point, wherein said sampler remains stationary during movement of said connecting device between said first and second positions, said sampler is attached to said connecting device, and including first valve means operable when said connecting device is moved to said second position for venting any pressure of product within said shell and for checking the integrity of said seal means, and second valve means operable when said connecting device is moved to said second position for venting any pressure of product within said sampler and for checking the integrity of said seal means.

13. A sampling apparatus, comprising:

a sampler operable to obtain discrete samples of liquid product from an interior of a vessel, said sampler including a plunger having a sample receiving recess;

a connecting device for coupling said sampler to the vessel, wherein said sampler is attached to said connecting device and said connecting device is movable between a first position placing said sampler into communication with the interior of the vessel and product therein and a second position taking said sampler out of communication with the interior of the vessel and product therein, said sampler being detachable from said connecting device, without escape of product from the vessel, when said connecting device is in said second position;

means for reciprocating said sampler plunger, when said connecting device is in said first position, to extend said plunger and recess through said connecting device and into the product in the vessel interior to receive in said recess a predetermined volume sample of product, and to then retract said plunger and recess from the vessel interior and through said connecting device to deliver the predetermined volume product sample in said recess to a sample collection point in said sampler;

means for continuously maintaining a seal between the interior of the vessel and said sample collection point during reciprocation of said plunger; and valve means operable when said connecting device is moved to said second position for venting any pressure of product within said sampler, wherein said sampler remains stationary during movement of said connecting device between said first and second positions.

14. A sampling apparatus as in claim 13, including further valve means operable when said connecting device is moved to said second position for venting any pressure of product within said connecting device.

* * * * *